United States Patent [19]

Kelton et al.

[11] 4,284,602
[45] Aug. 18, 1981

[54] INTEGRATED FLUID MANIPULATOR

[75] Inventors: Arden A. Kelton, Westminster; William P. Waters, Newport Beach; David G. Shrunk, Poway; Michael L. Bell, Hacienda Heights, all of Calif.

[73] Assignee: Immutron, Inc., Newport Beach, Calif.

[21] Appl. No.: 101,807

[22] Filed: Dec. 10, 1979

[51] Int. Cl.³ .................. B04B 5/12; G01N 21/07
[52] U.S. Cl. .................. 422/72; 233/26; 356/246
[58] Field of Search .............. 233/26; 422/72; 356/246

[56] References Cited

U.S. PATENT DOCUMENTS

| 3,899,296 | 8/1975 | Mailen et al. | 422/72 X |
| 3,901,658 | 8/1975 | Burtis et al. | 422/72 X |

Primary Examiner—Arnold Turk
Attorney, Agent, or Firm—Mahoney & Schick

[57] ABSTRACT

A rotatable element for use in centrifugal chemical-medical analysis apparatus wherein inlet means is provided in the element near the center of rotation thereof and an outlet is provided near the marginal radially outward edge thereof. A measuring chamber is provided intermediate the inlet and outlet and a conduit is afforded to such chamber from the inlet. A passageway is provided in the element extending radially inwardly from the chamber to a predetermined point or position relative to such chamber, and then to an overflow outlet to thereby define a predetermined filling level for the chamber.

Fluid entering the inlet of the rotating element flows simultaneously into the chamber and the passageway under the centrifugal force, the fluid at said predetermined point relative to said measuring chamber overflowing to thereby define the filling level in the chamber.

4 Claims, 5 Drawing Figures

INTEGRATED FLUID MANIPULATOR

The present invention relates generally to chemical-medical analysis apparatus, but more particularly to such machines or devices which are substantially automatic in their operation and analysis of certain chemical information.

Within recent years, several different types of automatic equipment for performing laboratory analyses have been provided. Such equipment has been particularly useful in the medical profession where it is necessary to perform various different kinds of chemical analyses within a very short period of time in order to properly and quickly diagnose a patient's condition. Such automatic chemical analyzing equipment also has important application to various other types of professions and industries where chemical procedures can be standardized and wherein it is desirable, if not mandatory, to provide quick and meaningful information.

Some prior automatic equipment or apparatus of this nature have utilized the centrifugal forces and effects which are found in centrifuges of various different types and kinds. As such, a fluid sample or fluid substance is rotated in a test tube or the like thereby creating centrifugal forces on the fluid.

Such prior art equipment has been very limited, however, due to the use of only very limited techniques. Therefore, such equipment has been incapable of performing certain important laboratory procedures.

It is contemplated that the present invention will provide chemical-medical analyzing equipment which is substantially automatic and which can perform a myriad of different chemical analyses within a very short period of time. By virtue of the present invention, fluids can be moved from one station or chamber to another, such that a very precise and accurate amount of fluid is provided in the right location for ensuring that only very accurate and precise laboratory procedures are performed.

It is an object of the present invention to provide in a centrifugal chemical-medical analysis apparatus, a rotatable element which is so constructed that a predetermined amount of fluid is substantially automatically provided at a specific reaction chamber without the need of any precise manual manipulations by the human operator of the apparatus.

Another object of the present invention is to provide a rotatable element for use in a centrifugal chemical-medical analysis apparatus as characterized above, which is capable of measuring and providing to a reaction chamber a precise amount of fluid provided an excessive amount of fluid is made available.

A still further object of the present invention is to provide a rotatable element for use in a centrifugal chemical-medical analysis apparatus as characterized above, wherein an overflow is provided for limiting the amount of fluid that can be provided to a given reaction chamber.

An even still further object of the present invention is to provide a rotatable element for use in a centrifugal chemical-medical analysis apparatus as characterized above, wherein a plurality of reaction chambers are connected together, each of such chambers being provided with a predetermined precise amount of fluid in accordance with the overflow means provided.

Another still further object of the present invention is to provide a rotatable element for use in a centrifugal chemical-medical analysis apparatus as characterized above, which can be charged with a predetermined amount of liquid or dry chemical in a reaction chamber to which can be applied, as desired, the predetermined precise amount of fluid to cause a very precise and accurate chemical reaction to take place without the need for highly skilled personnel.

Another still further object of the present invention is to provide in a rotatable element for use in a centrifugal chemical-medical analysis apparatus as characterized above, whch may be formed of plastic and which may be disposable.

Another object of the present invention is to provide a rotatable element for use in a centrifugal chemical-medical analysis apparatus as characterized above, which is simple and inexpensive to manufacture and which is rugged and dependable in operation.

The novel features which we consider characteristic of our invention are set forth with particularity in the appended claims. The invention itself, however, both as to its organization and mode of operation, together with additional objects and advantages thereof, will best be understood from the following description of specific embodiments when read in connection with the accompanying drawings, in which:

Like reference characters indicate corresponding parts throughout the several views of the drawings.

Figure 1:
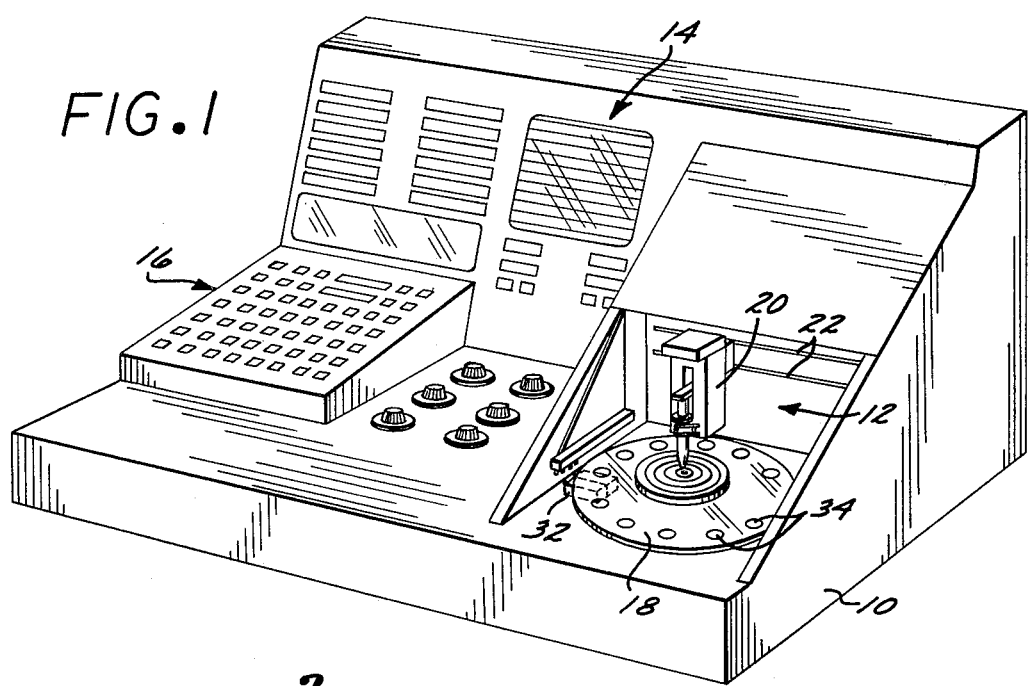
FIG. 1 is a perspective view of chemical-medical analysis apparatus according to the present invention.

Referring to FIG. 1 of the drawings, there is shown therein, apparatus 10 for performing substantially any type or kind of laboratory procedure, whether it be related to medicine or any other field or industry which employs chemical analyses. Such apparatus 10 comprises a procedures section 12, a read-out or display section 14, and a computer section 16. It is contemplated that chemical analyses will be performed in the procedures section 12, with the results of such procedures derived therefrom being displayed on a cathode ray tube or the like in the read-out section 14, and that suitable comparisons and other computer functions involving such information can be performed at section 16 to provide useful information for medical personnel or operators of chemical equipment.

The chemical analysis or procedures section 12 comprises a centrifuge which is capable of rotating a disc or element 18. As will hereinafter be explained in greater detail, it is contemplated that one or more automatic syringes, one of which is shown at 20, can be provided for substantially automatic injection of fluids into the disc 18. Such syringe 20 may be movable on suitable tracks or guide means, as shown at 22 in FIG. 1.

The disc or element 18 is constructed in a unique fashion so as to enable certain laboratory procedures to be performed automatically and in a relatively short period of time. In this regard, disc 18 is formed of inexpensive material such as any one of the many different plastics available today, but of such material which can be inexpensively but accurately machined or molded to provide the requisite chambers, passageways, conduits, and the like, as will hereinafter become more apparent. It is also contemplated that in the manufacture of such discs or elements 18, appropriate freeze-dried or granular chemicals can be added to and stored in the various cavities or chambers of the element to be available in the proper reaction chamber whenever the element is to be used to perform a certain chemical analysis or medical procedure. Thus, a medical or chemical laboratory would stock various different discs, precharged at the time of manufacture with different chemicals but in the precise amount, particularized to certain but different laboratory procedures to be performed. That is, each such disc would have one or more reaction provided with the appropriate chemicals so that when the disc is ultimately used, only appropriate fluids such as water, blood, contol fluids or the like would have to be added to complete the chemical reactions or laboratory procedures in a relatively automatic manner.

Figure 2:
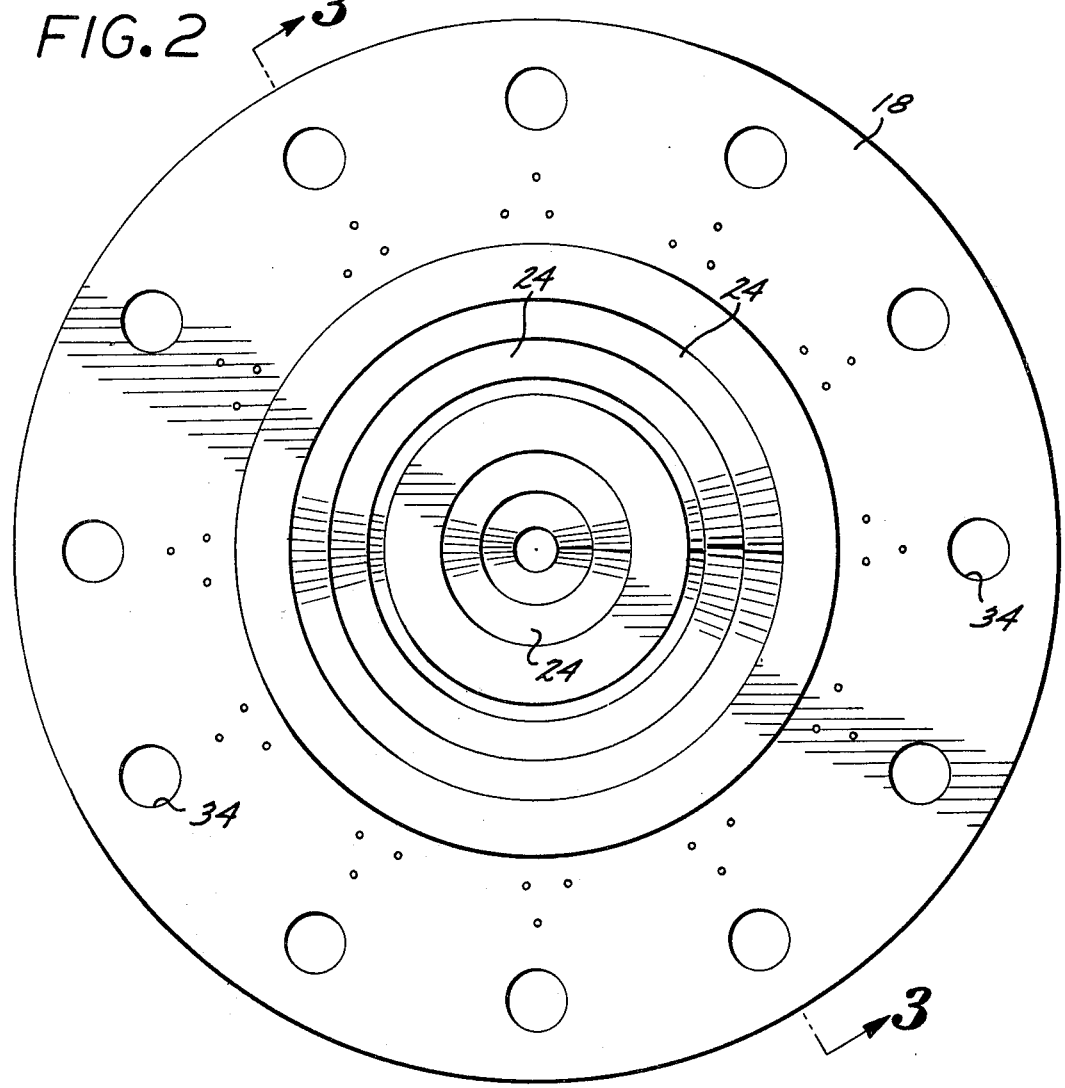
FIG. 2 is a top plan view of a disc or rotatable element for use in the apparatus of FIG. 1.
Figure 3:
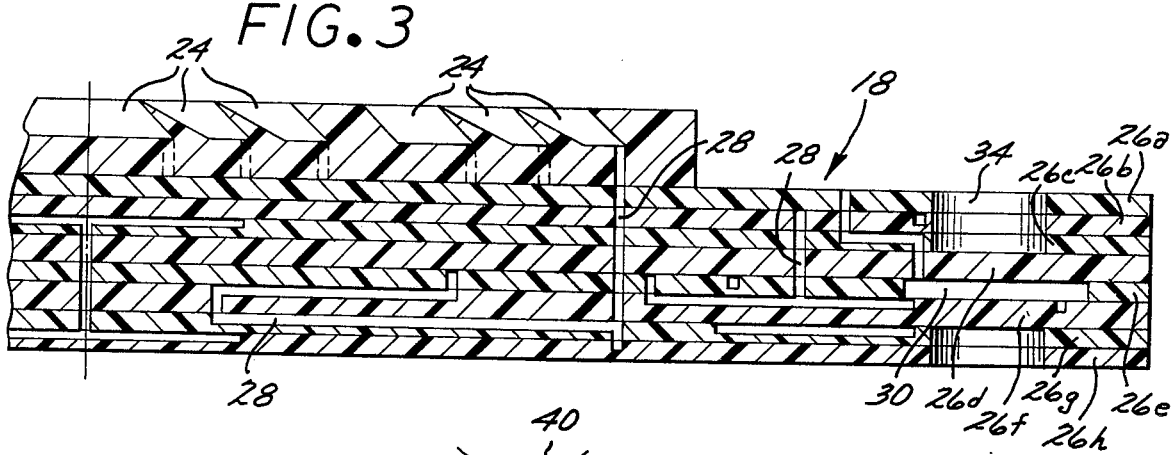
FIG. 3 is a fragmentary sectional view of the element taken substantially along line 3—3 of FIG. 2.

The central portion of the disc or element 18, as shown in FIG. 2 of the drawings, is formed with a plurality of concentric inlets as shown at 24. As seen in FIG. 3, the element 18 may be formed by bonding together several discs at 26a, 26b, 26c, 26d, 26e, 26f, 26g and 26h with each such disc being provided wth appropriate conduits or holes as shown at 28 leading from one or another of the inlets 24 to certain specific but independent chambers to enable a plurality of separate and independent chemical reactions or analyses to be performed in reaction chambers 30. The conduits or holes shown in the various discs in FIG. 3 and identified with the numeral 28 are merely illustrative of what can be provided in constructing the disc 18. On the other hand, it is well realized that element 18 can be formed as a single disc without the need for bonding or laminating together several discs as hereinbefore suggested. Ultimately, depending upon the chemical or medical laboratory procedure being performed, the results can be read with the appropriate automatic instruments, as shown at 32 in FIG. 1. The depressions or cavities 34 shown in FIGS. 2 and 3 enable such automatic readout instruments 32 to perform their intended function.

Figure 4:
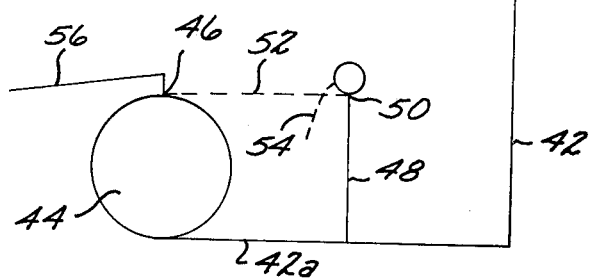
FIG. 4 is a diagrammatic showing of fluid measuring means used in the element.

The diagrammatic shown in FIG. 4 of the drawing is of a technique for substantially automatically filling a reaction chamber with the precise amount of fluid necessary for performing a given laboratory procedure. Therein is shown an inlet 40 which may be one of the concentric inlets 24 of FIGS. 2 and 3, and which communicates with an inlet conduit 42 which leads to a measuring chamber 44 which may have any desired shape, but which is shown in FIG. 4 as being generally circular. Inlet 40 is near the axis of rotation of the disc or element, which may resemble element 18 of FIGS. 2 and 3. Thus, when the element is caused to rotate centrifugal force causes, any fluid at the inlet 40 to flow radially outwardly of the element, down the conduit 42 as shown in FIG. 4. Such fluid passes through conduit 42a to fill the measuring chamber 44. An outlet near the top of chamber 44 is provided as shown at 46.

Also communicating with chamber 44, through conduit 42a, is a passageway 48, a portion of which extends radially inwardly from its connection with chamber 44 to a point shown at 50 in FIG. 4. At this point, the radially inward extension of passageway 48 terminates and then extends outwardly in the disc to an outlet. Thus, any excess fluid entering inlet 40 and filling conduits 42 and 42a, passageway 48 and chamber 44 is caused to spill over point 50 and pass to the outlet. This prevents such fluid from flowing radially inwardly beyond point 50 as well as a predetermined level within chamber 44 as defined by broken line 52 shown in FIG. 4.

This arrangement enables an excessive amount of fluid to be provided at inlet 40 by substantially any appropriate means as, for instance, the automatic syringe 20 of FIG. 1 or a manually operated pipette. With the disc 18 rotating, such fluid is forced radially outwardly of the disc, down conduit 42 to the bottom of chamber 44. Thus, the fluid level within chamber 44 continues to rise as long as an excessive amount of fluid is made available at inlet 40. At the same time, the fluid, such as blood, water or the like, rises within passageway 48 to the point 50, and within chamber 44 to broken line 52. When such conditions are reached, excessive fluid spills over the upper end of passageway 48 and is disposed of through the outlet (not shown in FIG. 4). Thus, regardless of the amount of excessive fluid afforded at inlet 40, only the predetermined precise amount of fluid is provided within chamber 44.

Various of the chambers, conduits and passageways in the diagram of FIG. 4 must be vented to atmospheric conditions external of disc 18 in order to enable such fluids to move freely therewithin. Thus, as shown diagrammatically at 54, such venting would be provided in the form of suitable openings from the various chambers and passageways to the atmosphere or an appropriate sealed plenum.

It is contemplated that chamber 44 could be a reaction chamber wherein certain appropriate chemicals had been provided so that upon introduction of the fluid, the appropriate chemical reaction would take place. On the other hand, chamber 44 might merely be a measuring chamber wherein the precise amount of fluid would be established, thereafter to be moved to an appropriate reaction chamber containing the appropriate predetermined amount of chemicals. In this regard, after the chamber 44 is provided with fluid to the level of broken line 52 as previously described, a liquid of heavier density, such as fluorocarbon, immiscible with the original fluid is introduced to the disc at inlet 40. Under the effects of the centrifugal force, the heavier density fluid flows down the conduit 42 and into the chamber 44, pushing the lighter density fluid out of the chamber through outlet conduit 56. That is, since such additional fluid is heavier than the previously-provided fluid in chamber 44, the lighter fluid is moved radially inwardly of the disc 18 and through the outlet conduit 56 to the appropriate reaction chamber (not shown in FIG. 4). As will be well understood by those persons skilled in the art, if the two fluids are immiscible they will remain separated throughout such procedure.

It should be noted that only a precise amount of such lesser density fluid is moved through the outlet conduit 56 since any excess amount of the heavier fluid flows into the outlet (not shown) through the passageway 48. Thus, by forming chamber 44 with a precise set of dimensions and hence a precise volume, and by forming conduit 42a with precise length and diameter, a correspondingly precise amount of fluid is moved through outlet conduit 56 to ensure that an accurate chemical reaction ultimately takes place.

Figure 5:
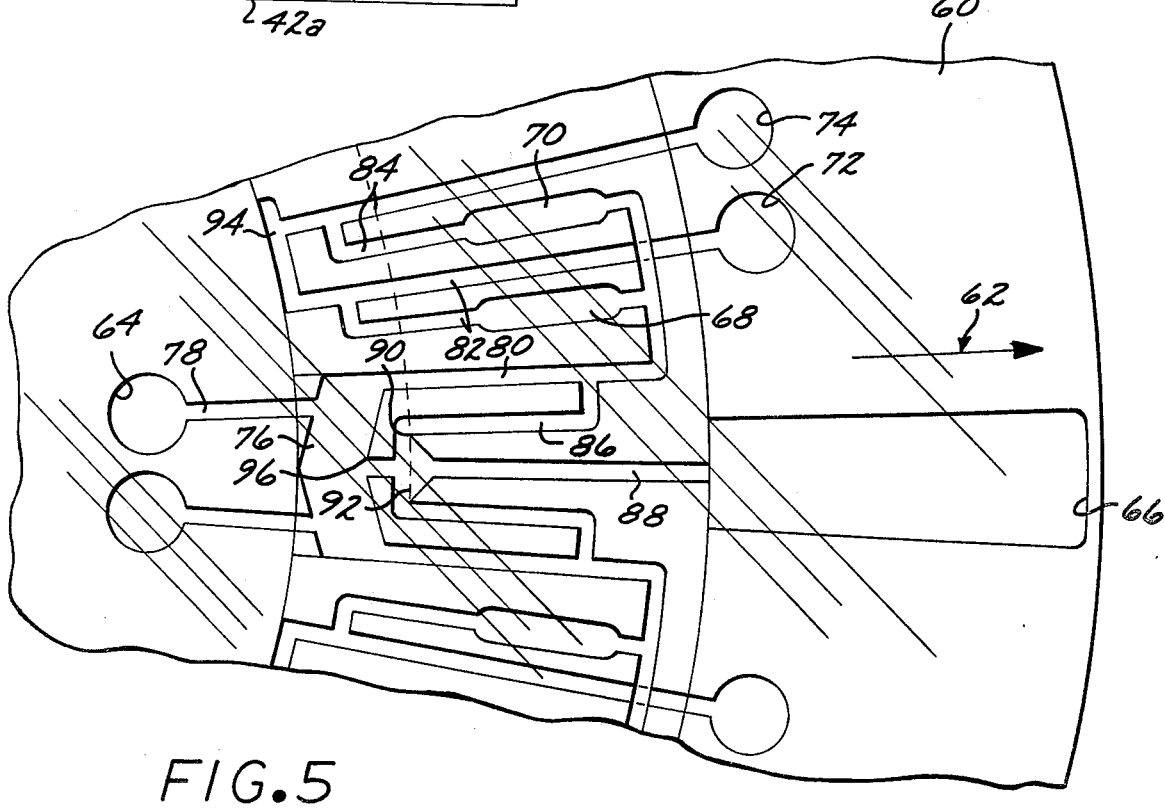
FIG. 5 is a fragmentary plan view of a preferred embodiment utilizing the fluid measuring techniques of FIG. 4.

Referring to FIG. 5 of the drawings, there is shown therein a preferred or practical embodiment of the present invention, utilizing the fluid measuring and manipulation techniques shown in FIG. 4 and as above explained.

With the disc or element 60 rotating about an axis which is to the left of FIG. 5 and which is at right angles to the paper, a centrifugal force is generated in the radially outward direction, as depicted by the arrow 62. An inlet chamber is provided at 64 and a relatively large outlet chamber is provided at 66. Both such chambers are vented to the atmosphere, although outlet chamber 66 could extend through the outer extremity or marginal edge of disc 60 so that all excess fluid would be automatically discharged from the disc upon reaching the outlet.

Intermediate the inlet 64 and the outlet 66 are a pair of measuring chambers 68 and 70 which provide a precise amount of fluid to reaction chambers 72 and 74, respectively.

An intermediate chamber 76 is provided as shown, a conduit affording fluid flow from the inlet 64 to such intermediate chamber and a conduit 80 being provided for conducting fluid from such intermediate chamber 76 to the lower or outer extremeties of measuring chambers 68 and 70. To move the fluid out of such measuring chambers, generally U-shaped outlet conduits 82 and 84 are provided between chamber 68 and chamber 72 and between chambers 70 and 74, respectively.

To provide the precise measurement, there is provided an overflow passageway 86 which connects with an outlet passageway 88 at a predetermined point 90.

With the disc or element 60 rotating, fluid is forced radially outwardly in the direction of arrow 62, from the inlet 64 through conduit 78, intermediate chamber 76 and conduit 80 to the measuring chambers 68 and 70. Such fluid fills the measuring chambers as well as the outlet passageways 82 and 84 therefrom to a level indicated by the broken line 92, under which conditions, any excess fluid spills over point 90 and flows through passageway 88 to outlet chamber 66. Thus, a precise amount of fluid is provided in the measuring chambers and conduits connected therewith.

Thereafter, by adding a heavier fluid to inlet 64, the centrifugal force pushes the lighter fluid in chambers 68 and 70 through conduits 82 and 84, respectively, so that the reaction chambers 72 and 74 are individually provided with a precise volume of fluid. Any excess heavier fluid flows through the overflow passageways 86 and 88 to the outlet 66. The appropriate chemical reactions then take place in the chambers 72 and 74, as above explained with respect to the diagrammatic showing in FIG. 4.

The conduits 82 and 84 are vented to the atmosphere through appropriate vent openings shown generally at 94. Also, auxilliary overflow means is provided through intermediate chamber 76 to compensate for possible unusually fast flow of fluid from inlet chamber 64 to the measuring chambers 68 and 70. That is, in the event such fluid moves inordinately fast as compared to the diameter of the conduit 80 leading to the chambers 68 and 70, and backup of fluid will spill over the point 96 in the intermediate chamber 76 rather than allowing fluid to be forced into the reaction chambers 72 and 74.

It is contemplated that the present invention enables the design of any appropriate number of measuring chambers and reaction chambers, as well as the formation of various different analyses stations around the periphery of the disc 18 or 60. In this regard, it is seen that disc 18 of FIG. 2 shows twelve different reaction stations equiangularly spaced about the periphery thereof. It is contemplated that each such station could be supplied separately and independently with appropriate fluids by having the inlets 24, as shown in FIGS. 2 and 3, connected individually to separate stations.

After the appropriate laboratory procedures have been performed, the disc 18 is stopped and the various test stations are read by the automatic read-out apparatus shown at 32 in FIG. 1.

It is thus seen that the present invention provides means in a centrifugal chemical-medical analysis apparatus for controlling or measuring the precise amount of fluid used in a given chemical reaction, without the need for any special skills or manual dexterity on the part of human operators associated with the centrifugal apparatus. Further, it ensures and provides for the transferring of such precise amount of fluid from one chamber or location to another to ensure that the proper and precise reaction takes place.

Although we have shown and described certain specific embodiments of our invention, we are well aware that many modifications thereof are possible. Our invention, therefore, is not to be restricted except insofar as is necessitated by the prior art and the spirit of the appended claims.

We claim:

1. In centrifugal chemical-medical analysis apparatus, the combination of: a rotatable element adapted to be mounted on and rotated by a suitable machine, said element being formed with fluid inlet means; means forming a measuring chamber in said element radially outwardly of said inlet means and conduit means interconnecting said inlet means and said measuring chamber; said element being further formed with a vented fluid outlet means from said measuring chamber; a passageway connected to said conduit means and in communication with said measuring chamber through said conduit means; and overflow outlet means communicating with said passageway, said overflow outlet means being radially located with respect to said measuring chamber to control the filling level in said measuring chamber.

2. In centrifugal chemical-medical analysis apparatus, the combination according to claim 1 wherein said vented fluid outlet means communicates with said measuring chamber radially inwardly of said filling level.

3. In centrifugal chemical-medical analysis apparatus, the combination according to claim 2 wherein said conduit means interconnects with said measuring chamber near the radially outward extremity of said chamber.

4. In centrifugal chemical-medical analysis apparatus, the combination according to claim 3 wherein two or more measuring chambers are provided in communication with said conduit means whereby each of said chambers is filled to the same filling level from the common conduit means as determined by the location of said overflow outlet means and wherein each of said measuring chambers with vented fluid outlet means.

* * * * *